US00PP19427P2

(12) United States Plant Patent
Korlipara

(10) Patent No.: US PP19,427 P2
(45) Date of Patent: Nov. 4, 2008

(54) ***ECHINACEA* PLANT NAMED 'TOMATO SOUP'**

(50) Latin Name: ***Echinacea* spp.**
Varietal Denomination: Tomato Soup

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/986,115

(22) Filed: Nov. 19, 2007

(51) Int. Cl.
*A01H 5/00* (2006.01)

(52) U.S. Cl. ..... Plt./428

(58) Field of Classification Search ..... Plt./428
See application file for complete search history.

*Primary Examiner*—Annette H Para
*Assistant Examiner*—S. B. McCormick-Ewoldt
(74) *Attorney, Agent, or Firm*—Klarquist Sparkman, LLP

(57) ABSTRACT

A new and distinct *Echinacea* plant named 'Tomato Soup' characterized by very large, bright red-orange flowers, well-branched upright flower stalks, and excellent vigor.

1 Drawing Sheet

Botanical denomination: *Echinacea* spp.
Variety designation: 'Tomato Soup'.

The present invention relates to a new and distinct cultivar of *Echinacea* and given the cultivar name 'Tomato Soup'. *Echinacea* is in the family Asteraceae. This new cultivar originated as a fourth-generation seedling from a planned breeding program using the parents *Echinacea paradoxa* (unpatented) and *Echinacea purpurea* 'Ruby Giant' (unpatented) for the initial cross. The exact parents of this selection are unnamed proprietary, unreleased plants.

This new *Echinacea* cultivar is distinguished by:

1. Very large, bright red-orange flowers
2. Well-branched upright flower stalks
3. Excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
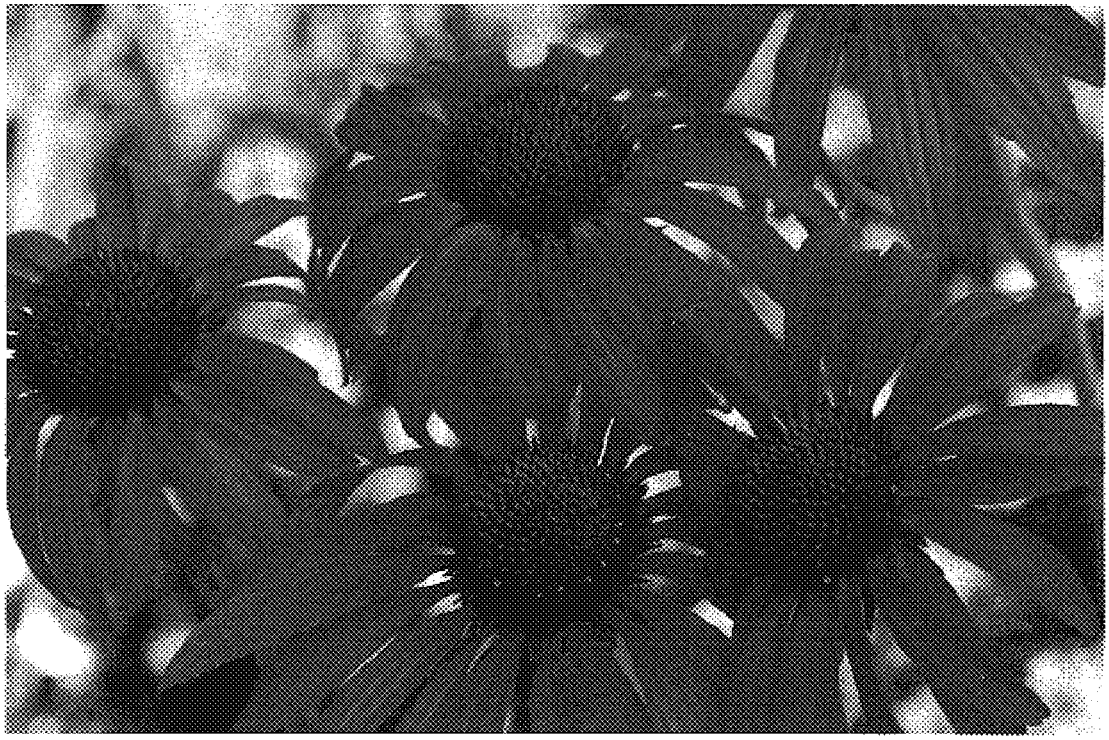
FIG. 1 shows the flowers of *Echinacea* 'Tomato Soup' cut from a plant growing in the ground in full sun in the field in late summer in Canby, Oreg.

The following is a detailed description of the new *Echinacea* cultivar based on observations of a 9-month-old specimen growing in the ground in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—70 cm wide and 80 cm tall to top of flowers.
- *Form.*—Basal clump.
- *Vigor.*—Excellent.
- *Roots.*—Fibrous, with many downward growing and few laterals, ivory in color, Yellow White 158D, roots develop easily from cuttings from the crown.

Stem (flowering):
- *Type.*—Ascending.
- *Size.*—Branching to 80 cm tall to a terminal flower and 1.3 cm wide at base.
- *Internode length.*—2 cm to 15 cm.
- *Surface texture.*—Strigose.
- *Color.*—Yellow Green 146C mottled with Yellow Green 144A.

Leaf (basal and stem):
- *Type.*—Simple.
- *Shape.*—Lanceolate.
- *Arrangement.*—Basal, stem leaves alternate.
- *Blade size.*—Grows to 17.5 cm long and 4 cm wide.
- *Margins.*—Entire.
- *Apex.*—Acuminate.
- *Base.*—Attenuate, continuing down petiole, clasping.
- *Surface texture.*—Strigose on both sides.
- *Venation.*—Pinnate.
- *Color.*—Topside, Yellow Green 147A with the vein Yellow Green 147D and bottom side Yellow Green 147A with the vein Yellow Green 147D.
- *Petiole description.*—Grows to 10 cm long and 3 mm wide, strigose, Yellow Green 147C.

Inflorescence:
- *Type.*—Composite on terminal stalked heads.
- *Number of flowering stems per plant in summer.*—4 to 7.
- *Flowering stem.*—Grows to 80 cm tall from the base of the plant to the terminal flower and can grow to 34 cm long from the top leaf to the base of a flower head; may branch 5 to 11 times; diameter growing to 10 mm wide near the flower head; strigose, branched, with two to five branches, Yellow Green 145C mottled with Yellow Green 146B.

*Size.*—Grows to 15.5 cm wide and 4.5 cm deep as disc enlarges.

*Form.*—Ray petals cup downward slightly, mature disc is conic.

*Immature inflorescence.*—4 cm wide and 3 cm deep, ray florets held at a 45 degree angle and rolled-up so only the back color shows, Greyed Purple 185B except on inside tip where Yellow 2D, disc is Green 137A in background with the foreground Greyed Purple 187A.

*Ray florets.*—Without pistil or stamen, 21 to 29 in number, each oblanceolate to lanceolate with the tip two toothed, entire margins, base attenuate, grows to 5 cm long and 12 mm wide, glabrous on both sides; topside color of young ray florets Red 45A lightening to Red 44A and finally fading to Greyed Orange 167A on top half and blending to Red 53B at the base, bottom side color Greyed Purple 186A to 186C.

*Disc.*—Flat becoming conic, 4 cm long and becoming 4.3 cm wide with maturity, overall color Brown 200A.

*Disc florets.*—About 400 in number, each 14 mm long and 1.5 mm wide, each with one persistent, very stiff bract (12 mm long and Greyed Purple 187A on tip to Greyed Purple 185A below the tip, Yellow Green 144A to 144D on bottom half); corolla 5 mm long and 1.5 mm wide, 5 lobed, glabrous, Yellow Green 144A; pistil 12 mm long, ovary 3 mm long White 155D, style 6 mm long, Yellow Green 154D, with an extruding, 2-branched stigma, spreading 3.5 mm wide, Greyed Purple 187A; stamen 4 in number, 5 mm long, anthers 3 mm long and Black 201A, filaments 2 mm long, Yellow White 158C, pollen Yellow Orange 17A.

*Phyllaries.*—In 4 leafy series, area 3.7 cm wide and 20 mm deep, lobes lanceolate in shape, reflexed, grow to 20 mm long and 3 mm wide, Yellow Green 147B, margins strigose, tip acute.

*Receptacle.*—Grows to 17 mm wide and 22 mm deep, White 155D.

*Bloom period.*—July through October in Canby, Oreg.

*Fragrance.*—Lovely, floral.

*Bloom time.*—Summer until frost in Canby, Oreg.

*Lastingness.*—Each inflorescence lasts about two weeks in Canby, Oreg.

Seeds: Average number of 10 seeds/head, each 6 mm long and 2.5 mm wide, oval, Grey Brown 199C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

COMPARISONS TO SIMILAR *ECHINACEA*

Compared to *Echinacea* 'Ruby Giant' (unpatented), the original seed parent in the breeding line, the new variety has red-orange rather than red-purple flowers.

Compared to *Echinacea paradoxa,* an unpatented plant and the original pollen parent in the breeding line, the new variety is shorter, red-orange rather than yellow, with more ray florets, and with ray florets slightly rather than strongly reflexed.

Compared to *Echinacea* 'Sunset' (U.S. Plant Pat. No. 16,424), the new variety has larger and brighter red-colored ray florets.

I claim:

1. A new and distinct *Echinacea* plant as herein illustrated and described.

* * * * *